United States Patent
Cox et al.

(10) Patent No.: US 7,612,871 B2
(45) Date of Patent: Nov. 3, 2009

(54) FREQUENCY-MULTIPLEXED DETECTION OF MULTIPLE WAVELENGTH LIGHT FOR FLOW CYTOMETRY

(75) Inventors: James A. Cox, New Brighton, MN (US); J. David Zook, Golden Valley, MN (US)

(73) Assignee: Honeywell International Inc, Morristown, NJ (US)

(*) Notice: Subject to any disclaimer, the term of this patent is extended or adjusted under 35 U.S.C. 154(b) by 784 days.

(21) Appl. No.: 10/931,686

(22) Filed: Sep. 1, 2004

(65) Prior Publication Data
US 2006/0051096 A1    Mar. 9, 2006

(51) Int. Cl.
*G01C 3/08* (2006.01)
*G01N 21/00* (2006.01)
(52) U.S. Cl. .................. 356/4.01; 356/28; 422/82.05
(58) Field of Classification Search ............. 356/4.01, 356/28, 28.5, 39, 337, 342; 422/82.05
See application file for complete search history.

(56) References Cited

U.S. PATENT DOCUMENTS

| | | | |
|---|---|---|---|
| 3,822,095 A | 7/1974 | Hirschfeld | |
| 3,976,862 A | 8/1976 | Curbelo | |
| 4,478,076 A | 10/1984 | Bohrer | |
| 4,478,077 A | 10/1984 | Bohrer | |
| 4,501,144 A | 2/1985 | Higashi et al. | |
| 4,651,564 A | 3/1987 | Johnson et al. | |
| 4,661,913 A | 4/1987 | Wu et al. | |
| 4,662,742 A | 5/1987 | Chupp | |
| 4,683,159 A | 7/1987 | Bohrer et al. | |
| 4,695,034 A | 9/1987 | Shimizu et al. | |
| 4,745,279 A | 5/1988 | Karkar et al. | |
| 4,765,737 A | 8/1988 | Harris et al. | |
| 4,786,165 A | 11/1988 | Yamamoto et al. | |
| 4,817,101 A | 3/1989 | Wyeth et al. | |
| 4,874,949 A | 10/1989 | Harris et al. | |
| 4,905,169 A | 2/1990 | Buican et al. | |
| 4,911,616 A | 3/1990 | Laumann, Jr. | |
| 4,953,978 A | 9/1990 | Bott et al. | |
| 4,957,363 A | 9/1990 | Takeda et al. | |
| 5,050,429 A | 9/1991 | Nishimoto et al. | |
| 5,078,581 A | 1/1992 | Blum et al. | |
| 5,082,242 A | 1/1992 | Bonne et al. | |
| 5,085,562 A | 2/1992 | van Lintel | |

(Continued)

FOREIGN PATENT DOCUMENTS

EP    1001326    5/1999

(Continued)

OTHER PUBLICATIONS http://www.micronics.net/tsensor.htm, pp. 1-4, downloaded Jun. 14, 2000.

(Continued)

*Primary Examiner*—Isam Alsomiri
(74) *Attorney, Agent, or Firm*—Kris T. Fredrick

(57) ABSTRACT

A multiplexed set of light sources having outputs of light with various wavelengths which are combined into one beam. The beam may impinge a particle in a flow channel of a cytometer. The light leaving the flow channel may be sensed by a detector and the light distinguished according to wavelength.

18 Claims, 3 Drawing Sheets

U.S. PATENT DOCUMENTS

| | | |
|---|---|---|
| 5,096,388 A | 3/1992 | Weinberg |
| 5,108,623 A | 4/1992 | Cangelosi et al. |
| 5,129,794 A | 7/1992 | Beatty |
| 5,171,132 A | 12/1992 | Miyazaki et al. |
| 5,176,358 A | 1/1993 | Bonne et al. |
| 5,185,641 A | 2/1993 | Igushi et al. |
| 5,194,909 A | 3/1993 | Tycko |
| 5,219,278 A | 6/1993 | van Lintel |
| 5,224,843 A | 7/1993 | van Lintel |
| 5,239,352 A * | 8/1993 | Bissonnette ............... 356/5.01 |
| 5,244,537 A | 9/1993 | Ohnstein |
| 5,250,810 A | 10/1993 | Geiger |
| 5,323,999 A | 6/1994 | Bonne et al. |
| 5,351,121 A | 9/1994 | Baer et al. |
| 5,363,222 A | 11/1994 | Ledebuhr |
| 5,367,474 A | 11/1994 | Auer et al. |
| 5,441,597 A | 8/1995 | Bonne et al. |
| 5,452,878 A | 9/1995 | Gravesen et al. |
| 5,504,337 A | 4/1996 | Lakowicz et al. |
| 5,528,045 A | 6/1996 | Hoffman et al. |
| 5,540,494 A | 7/1996 | Purvis, Jr. et al. |
| 5,570,193 A | 10/1996 | Landa et al. |
| 5,601,080 A | 2/1997 | Oppenheimer |
| 5,616,501 A | 4/1997 | Rodriguez |
| 5,633,724 A | 5/1997 | King et al. |
| 5,683,159 A | 11/1997 | Johnson |
| 5,684,575 A | 11/1997 | Steen |
| 5,716,852 A | 2/1998 | Yager et al. |
| 5,726,751 A | 3/1998 | Altendorf et al. |
| 5,757,476 A | 5/1998 | Nakamoto et al. |
| 5,793,485 A | 8/1998 | Gourley |
| 5,799,030 A | 8/1998 | Brenner |
| 5,822,170 A | 10/1998 | Cabuz et al. |
| 5,824,269 A | 10/1998 | Kosaka et al. |
| 5,836,750 A | 11/1998 | Cabuz |
| 5,837,547 A | 11/1998 | Schwartz |
| 5,863,502 A | 1/1999 | Southgate et al. |
| 5,880,474 A | 3/1999 | Norton et al. |
| 5,893,722 A | 4/1999 | Hibbs-Brenner et al. |
| 5,901,939 A | 5/1999 | Cabuz et al. |
| 5,922,210 A | 7/1999 | Brody et al. |
| 5,932,100 A | 8/1999 | Yager et al. |
| 5,948,684 A | 9/1999 | Weigl et al. |
| 5,971,158 A | 10/1999 | Yager et al. |
| 5,972,710 A | 10/1999 | Weigl et al. |
| 5,974,867 A | 11/1999 | Forster et al. |
| 5,994,089 A | 11/1999 | Siiman et al. |
| 6,007,775 A | 12/1999 | Yager |
| 6,032,689 A | 3/2000 | Tsai et al. |
| 6,082,185 A | 7/2000 | Saaski |
| 6,097,485 A | 8/2000 | Lievan |
| 6,106,245 A | 8/2000 | Cabuz |
| 6,109,889 A | 8/2000 | Zengerle et al. |
| 6,139,800 A | 10/2000 | Chandler |
| 6,154,276 A | 11/2000 | Mariella, Jr. |
| 6,179,586 B1 | 1/2001 | Herb et al. |
| 6,184,607 B1 | 2/2001 | Cabuz et al. |
| 6,215,221 B1 | 4/2001 | Cabuz et al. |
| 6,237,619 B1 | 5/2001 | Maillefer et al. |
| 6,240,944 B1 | 6/2001 | Ohnstein et al. |
| 6,249,341 B1 | 6/2001 | Basiji et al. |
| 6,281,975 B1 | 8/2001 | Munk |
| 6,382,228 B1 | 5/2002 | Cabuz et al. |
| 6,549,275 B1 | 4/2003 | Cabuz et al. |
| 6,597,438 B1 | 7/2003 | Cabuz et al. |
| 6,700,130 B2 | 3/2004 | Fritz |
| 2003/0002027 A1 | 1/2003 | Fritz |
| 2003/0030783 A1 | 2/2003 | Roche et al. |
| 2003/0054558 A1 | 3/2003 | Kurabayashi et al. |
| 2003/0142291 A1 | 7/2003 | Padmanabhan et al. |
| 2004/0036874 A1 | 2/2004 | Kramer |
| 2004/0263851 A1 * | 12/2004 | Dobbs et al. ............... 356/436 |
| 2005/0041249 A1 * | 2/2005 | Dobbs et al. ............... 356/364 |
| 2005/0100336 A1 * | 5/2005 | Mendenhall et al. ......... 398/27 |
| 2007/0165225 A1 * | 7/2007 | Trainer ...................... 356/335 |

FOREIGN PATENT DOCUMENTS

| | | |
|---|---|---|
| EP | 1491877 | 12/2004 |
| GB | 1237547 | 6/1971 |
| GB | 2212261 | 7/1989 |
| WO | WO95/27199 | 3/1995 |
| WO | WO99/60397 | 4/1999 |
| WO | WO01/09598 | 7/2000 |
| WO | 2005026673 | 3/2005 |

OTHER PUBLICATIONS http://www.micronics.net/hfilter.htm, pp. 1-3, downloaded Jun. 14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Differential Blood Cell Counts Obtained Using A Microchannel Based Flow Cytometer", Solid State Sensors & Actuators, vol. 1, 531, 1997.

Altendorf et al., "Microfabrication Technology For Research And Diagnostics, Silicon Microchannel Optical Flow Cytometry", SPIE Proceedings, Biomedical Optics 96, Jan. 1996.

Altendorf et al., "Results Obtained Using A Prototype Microfluidics-Based Hematology Analyzer", SPIE Biomedical Optics 97, 1997.

Cabuz, et al., "Mesoscopic Sampler Based on 3D Array of Electrostatically Activated Diaphragms", Transducers '99, The 10th International Conference on Solid-State Sensors and Actuators, Digest of Technical Papers, vol. 2, Jun. 7-10, 1999.

Darling et al., "Integration Of Microelectrodes With Etched Microchannels For In-Stream Electrochemical Analysis", MicroTAS 98, Banff, Canada, Apr. 1998.

Hatch et al., "Microfluidic Approaches To Immunoassays", SPIE conference on Micromachining and Microfabrication Symposium at Santa Clara, CA, Sep. 20-22, 1999.

Huang. et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10, No. 4, pp. 482-491, Dec. 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometry 9:39-43, 1988.

Weigl et al., "Silicon-microfabricated diffusion-based optical chemical sensor," Sensors and Actuators, B 38-39, pp. 452-457, 1997.

Weigl et al., "Diffusion-Based Optical Chemical Detection In Silicon Flow Structures", Analytical Methods & Instrumentation, μTTAS 96 special edition, 1996.

Weigl et al., "Microfluidic Diffusion-Based Separation And Detection", Science, vol. 283, pp. 346-347, Jan. 15, 1999.

Weigl et al., "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al., "Rapid Sequential Chemical Analysis Using Multiple Fluorescent Reporter Beads", μTTAS 96 Conference Proceedings, 1996.

Weigl et al., "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Weigl, et al., "Fluorescence and Absorbance Analyte Sensing In Whole Blood Based On Diffusion Separation In Silicon-Microfabricated Flow Structures," SPIE Proceedings, J. Lakowitz (ed.), Advances in Fluorescence Sensing Technology III, 1997, pp. 171-181.

Yager et al., "Design Of Microfluidic Sample Preconditioning Systems For Detection Of Biological Agents In Environmental Samples", SPIE Proceedings, 3515, 252-259, 1998.

Yager et al.,"Applying Microfluidic Chemical Analytical Systems To Imperfect Samples", Micro Total Analysis Systems 98, Kluwer Academic Publishers, Dordrecht, 207-212, 1998.

Dobbs et al., "Validation of Design for Space Based Tunable Diode Laser Absorption Spectroscopy Payload," Diode Lasers and Applications in Atmospheric Sensing, Proceedings of SPIE, vol. 4817, pp. 123-128, 2002.

\* cited by examiner

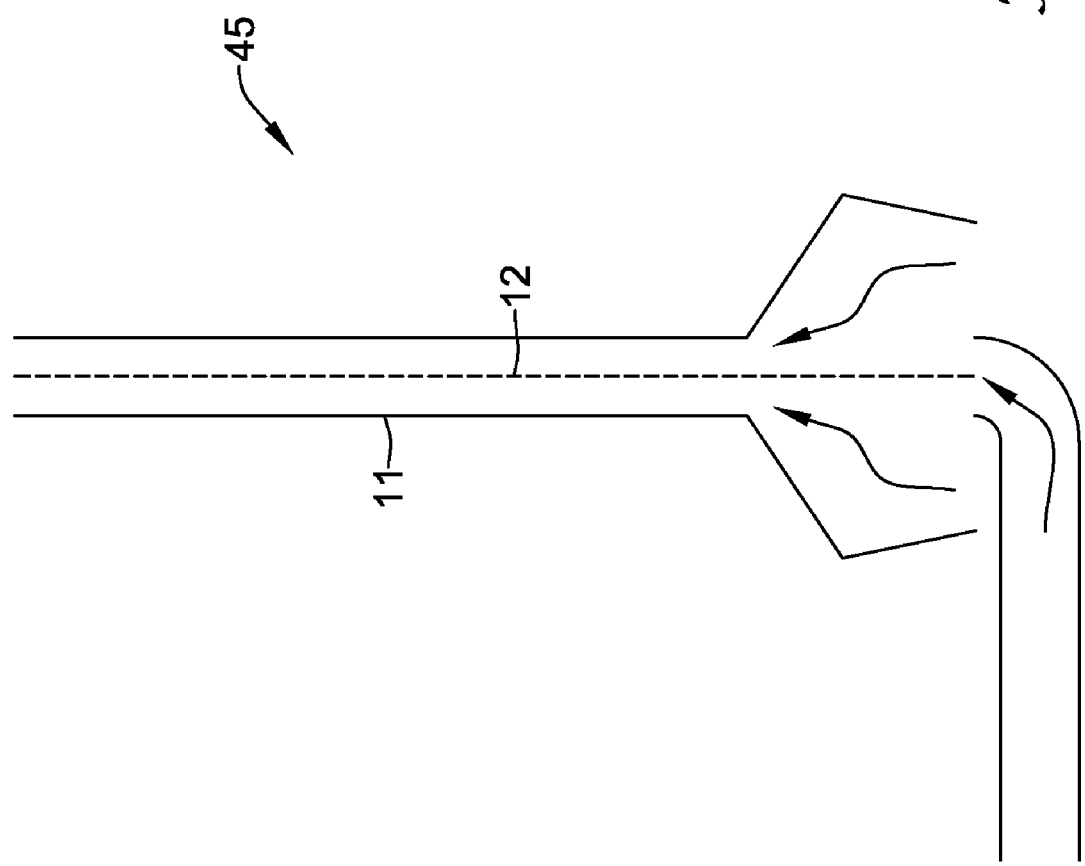

FREQUENCY-MULTIPLEXED DETECTION OF MULTIPLE WAVELENGTH LIGHT FOR FLOW CYTOMETRY

BACKGROUND

This invention pertains to cytometers and particularly to optical systems of cytometers. More particularly, the invention pertains to the optical acquisition of information about microscopic particles or components in a flow stream of a cytometer.

This invention is related to U.S. patent application Ser. No. 10/225,325, by Bernard Fritz et al., filed Aug. 21, 2002, and entitled "Optical Alignment Detection System", which is incorporated herein by reference; and the invention is related to U.S. patent application Ser. No. 10/304,773, to Aravind Padmanabhan et al., filed Nov. 26, 2002, and entitled "Portable Scattering and Fluorescence Cytometer", which is incorporated herein by reference. This invention also is related to U.S. Pat. No. 6,549,275 B1, by Cabuz et al., issued Apr. 15, 2003, and entitled "Optical Detection System for Flow Cytometry"; U.S. Pat. No. 6,597,438 B1, by Cabuz et al., issued Jul. 22, 2003, and entitled "Portable Flow Cytometer"; U.S. Pat. No. 6,382,228 B1, by Cabuz et al., issued May 7, 2002, and entitled "Fluid Driving System for Flow Cytometry"; U.S. Pat. No. 6,700,130 B2, issued Mar. 2, 2004, by Fritz, and entitled "Optical Detection System for Flow Cytometry"; and U.S. Pat. No. 6,240,944 B1, by Ohnstein et al., issued Jun. 5, 2001, and entitled "Addressable Valve Arrays for Proportional Pressure or Flow Control"; all of which are incorporated herein by reference. The term "fluid" may be used herein as a generic term that includes gases and liquids as species. For instance, air, gas, water and oil are fluids.

SUMMARY

The invention is an optical system for a cytometer using a multiplexing scheme to detect light of various wavelengths to obtain information relative to the particles that the light is impinging in a flow channel of the cytometer.

BRIEF DESCRIPTION OF THE DRAWING

FIG. 3 is a diagram of a cytometer as an illustrative example that may use the multiplexed multiple wavelength light scattering system.

DESCRIPTION

Improved performance (i.e., accuracy, selectivity, reliability, and so on) may be achieved by measuring optical scattering properties of a particle at multiple wavelengths. The invention may provide a way to accomplish this measuring approach by using a single detector assembly for all wavelengths. Each wavelength light source may be modulated at a unique frequency sufficiently separated from the other modulated sources to enable its signal to be demultiplexed unambiguously at the output of the detector. Light from all modulated sources scattered by the particle under measurement may be collected on the same detector assembly.

With flow cytometry, improved differentiation and accuracy in counting and distinguishing multiple particle types (e.g., blood cells) may be achieved by performing multi-dimensional measurements, such as particle volume, scattering at various angles, and scattering in various wavelengths. The invention may reveal improvements to this optical interrogation technique (i.e., multi-wave scattering). Scattering at multiple wavelengths may be done at spatially separated locations along the flow channel. This may require careful synchronization in timing as well as multiple detector arrays and spectra filters. This difficulty may be avoided by the use of modulation frequency multiplexing of the various wavelength sources. Each source may be modulated at a unique and sufficiently high frequency to meet system bandwidth requirements. The sources may be folded into one optical input path and focused simultaneously onto the same particle location. The scattered light at the various wavelengths may then be collected onto the same detector array to determine the angular information, and the signals at the different wavelengths may be separated by temporally filtering (e.g., Fourier transform methods) the detector signals.

Figure 1:
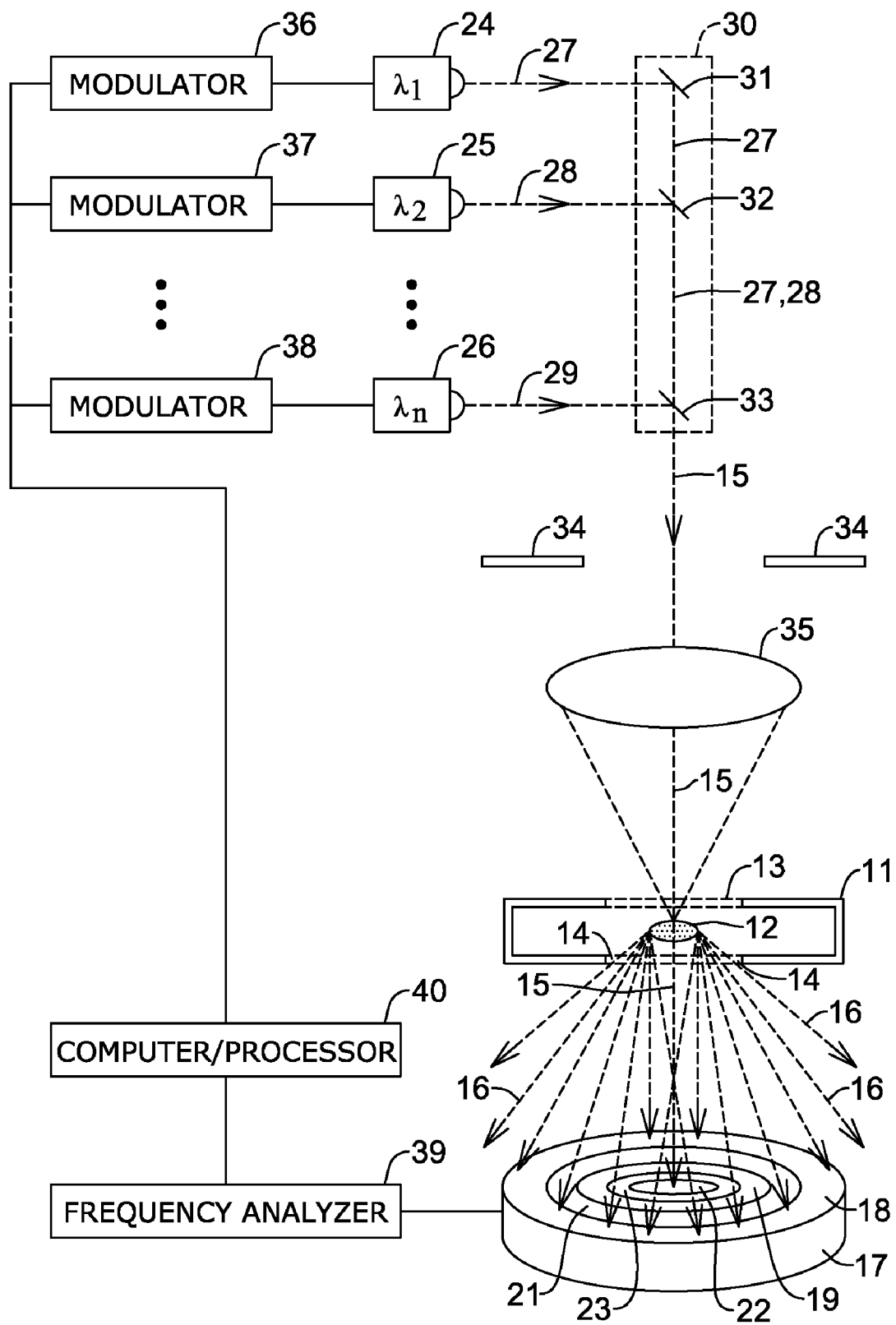
FIG. 1 shows a multiplexed multiple wavelength light scattering system with a single detector.

FIG. 1 shows an illustrative example implementing the invention. This figure shows a cross-section view of a channel 11. Channel 11 may be a flow or measurement channel of a cytometer. It may have a core stream having particles 12 moving through channel 11.

The core stream with particles 12 may be looked at as flowing into the surface of the figure. Channel 11 may be lengthy. The core stream along with particles 12 may be kept away from the inside surfaces of channel 11 with a sheathing fluid that surrounds the core stream. The location of the cross-section of channel 11 may be where a light source and detector arrangement may be placed. Channel 11 may have transparent windows 13 and 14 to facilitate the light source detector arrangement. A light beam 15 may enter channel 11 through window 13, impinge a particle 12 which may scatter beam 15 into light 16 which may exit channel 11 through window 14. Light 16 may be sensed by a detector 17. Detector 17 may be an annular type having a ring of surface area 18 sensitive to light. The detector 17 may be expanded with another ring of surface area 19 also sensitive to light 16. Light sensitive surfaces 18 and 19 may be isolated form each other by an annular area 21 that is not sensitive to light. Also, detector 17 may be further expanded with a central light-sensitive area 22 that may be isolated from the light-sensitive annular area 19 by an annular area 23 that is not sensitive to light. The detector 17 may be expanded to include as many annular detectors, each subtending its own prescribed angular interval, as needed. The annular detectors or other kinds of detectors of an array of the detector may provide electrical signals representing light impinging the detector at respective angles. That is, one electrical signal may represent detected light of a first angle; another electrical signal may represent detected light of a second angle; and so on.

Various kinds of information may be obtained about the particles 12 from the scattered light. First, a count of the particles 12 may be made with the successive interruption of the light beam 15 to detector 17. Other information about the size, shape, surface, and so on, about particles 12 may be obtained from scattered light that impinges detector 17. The magnitudes of the scattered light and the location of such light on detector 17 may be noted electronically from the signals from the various detector 17 surfaces. Another dimension of information may be obtained from the scattered light if the various wavelengths of the scattered light are known. Light 15 beams of various wavelengths may scatter differently from particles 12. That is, a light beam of one wavelength may scatter differently than a light beam of another wavelength for the same point of impingement of a particle, or even the same particle, in the same location. These differences of scattering may provide additional information about the particle.

To accomplish projecting a light beam 15 having various but identifiable frequencies of light may be achieved with the present invention. Beam 15 may be composed of light from a number (n) of light sources 24, 25 and 26. Light source 24 may emit or emanate a light beam 27 having a wavelength $\lambda_1$. Light source 25 may emanate a light beam 28 having a wavelength $\lambda_2$, and light source 26 may emanate a beam 29 having a wavelength $\lambda_n$. Between light source 25 and light source 26 may be numerous similar light sources with light beams having different wavelengths, respectively.

Beam 27 may propagate from source 24 to a component dichroic mirror 31 in a dichroic fold mirror assembly 30. Mirror 31 may reflect at least a portion of beam 27 approximately 90 degrees towards channel 11. Beam 28 may propagate to a dichroic mirror 32 of assembly 30. Mirror 32 may deflect and/or reflect at least a portion of beam 28 approximately 90 degrees towards channel 11. Beam 29 may propagate to a dichroic mirror 33 of assembly 30. Mirror 33 may reflect at least a portion of beam 29 approximately 90 degrees towards channel 11. There may be additional beams and mirrors between beams 28 and 29 and between mirrors 32 and 33, respectively.

As beam 27 propagates toward channel 11, it may, at least in part, go through mirrors 32 and 33 and any additional mirrors between those mirrors. Likewise, as beam 28 propagates toward channel 11, it may, at least in part, go through mirror 33 and any mirrors between mirrors 32 and 33. A resultant beam 15, which may include beams 27, 28 and 29 and any beams reflected or deflected by other mirrors situated between mirrors 32 and 33 of assembly 30. Beam 15 may proceed through aperture 34, optics 35 and window 13 of channel 11.

Since beam 15 may go through window 13 of channel 11, impinge a particle 12 and be scattered as light beams 16 that go through window 14 to the detector 17, there may be an interest to determine which wavelengths each of the light beams 16 has. The answer might not be evident in how to identify the wavelength or source of the reflected light in the electrical signals being output from detector 17.

To identify the wavelength of the detected light 16, scattered or unscattered, may be achieved with modulation of the light from each of the sources. That is, a modulator 36 may modulate the output of the light source 24 with a frequency $f_1$. Also, a modulator 37 may modulate the output of light source 25 with a frequency $f_2$ and modulator 38 may modulate the output of light source 26 with a frequency $f_n$. Between modulators 37 and 38 there may be other modulators that modulate additional light sources of other wavelengths that may be situated between light sources 25 and 26. This approach may be regarded as a frequency multiplexing of the light sources. Modulators 36, 37, 38 and the other modulators may be connected to and controlled by computer/processor 40.

The output of detector 17 may go to a frequency analyzer 39 which may demultiplex the detected light 16 and 15 signals and separate out the light into component signals according to their wavelengths and respective light sources. These signals may be provided to the computer/processor 40 for analysis, counting, identification, recording and/or other actions.

Figure 2:
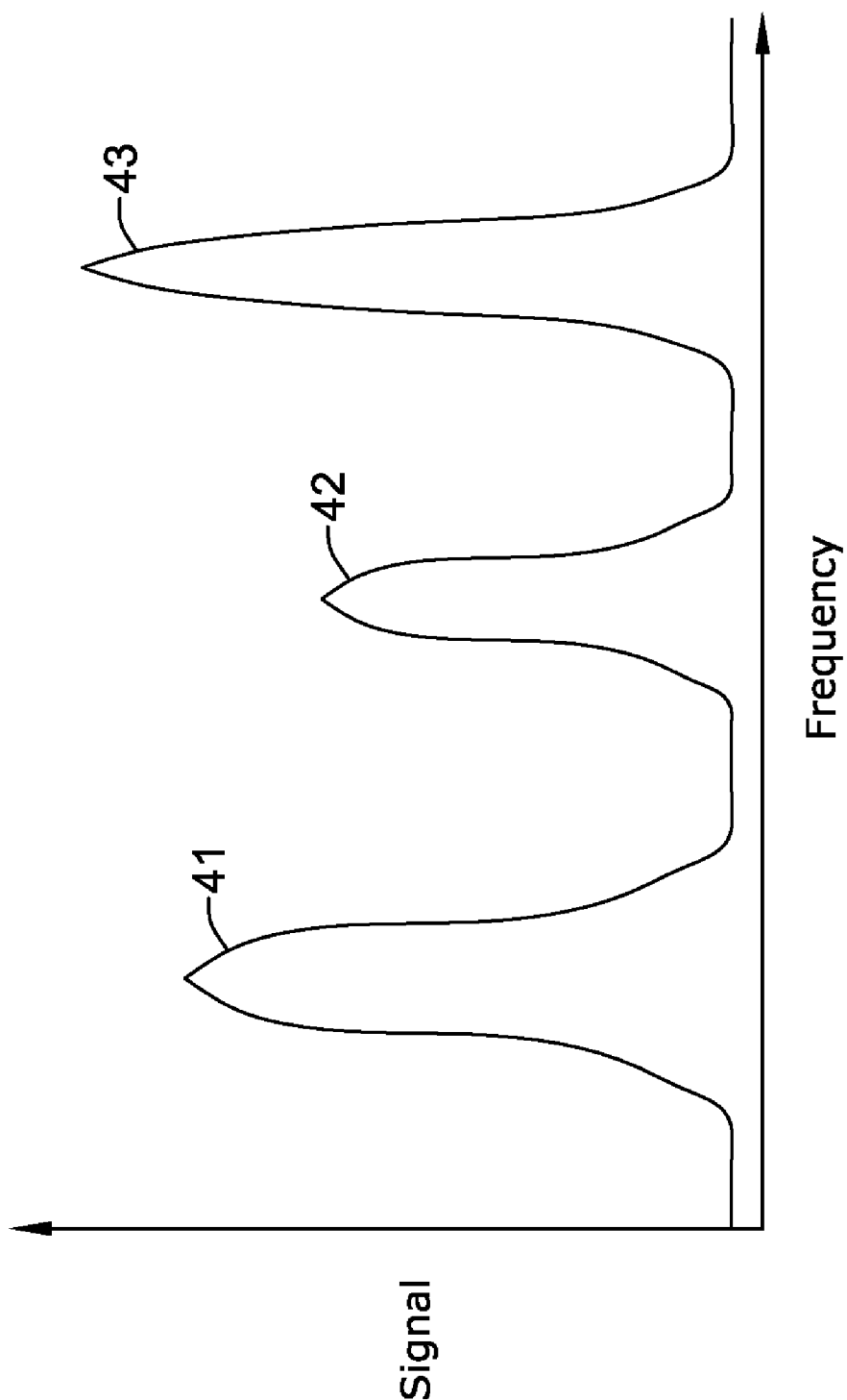
FIG. 2 is a graph of light signals versus their respective modulation frequencies.

Modulation frequencies may be relatively high in comparison to signal frequencies. FIG. 2 reveals a graph of the signals multiplexed according to frequency. As an illustrative example, a signal 41 may be of the wavelength $\lambda_1$ multiplexed at 10.0 MHz, a signal 42 may be of the wavelength $\lambda_2$ multiplexed at 10.3 MHz, and a signal 43 may be of the wavelength $\lambda_n$ multiplexed at 10.6 MHz. Additional signals of other wavelengths may be multiplexed at other frequencies for demultiplexing at the output of the detector 17.

FIG. 3 is a diagram of a cytometer 45 that may incorporate an illustrative application of the multiplexed multiple wavelength light scattering system. Cytometer 45 may have a channel 11 with a core stream of particles 12.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A multiple wavelength optical system comprising:
   a plurality of light sources;
   a frequency modulator connected to each light source;
   a dichroic fold mirror having an element proximate to each light source, and an output of light directed to a target;
   an array of annular light detectors proximate to the target; and
   a frequency analyzer connected to the light detector;
   wherein the annular light detectors are isolated from each other by an annular area that is not sensitive to light such that each annular detector subtends its own prescribed angle and the annular detectors provide an electrical signal representing light impinging the detector at respective angles.

2. The system of claim 1, wherein:
   at least one light source of the plurality of light sources emits light having a wavelength different than the wavelength of light emitted by another light source; and
   the at least one light source emits light modulated with a frequency different from a frequency that light emitted by another source is modulated with.

3. The system of claim 2, further comprising:
   a frequency analyzer connected to the array of detectors; and
   wherein signals caused by light emitted by the at least one light source of one wavelength of the plurality of light sources are distinguished from signals caused by light emitted by another light source of another wavelength of the plurality of light sources, by the frequency analyzer.

4. The system of claim 3, wherein the dichroic fold mirror folds light emitted by each light source of the plurality of light sources into one output of light directed to a target.

5. The system of claim 1, wherein the array of light detectors comprises an array of concentric annular detectors.

6. The system of claim 1, wherein the target is a core stream of a flow stream channel of a cytometer.

7. The system of claim 6, wherein the array of light detectors comprises a FALS detector.

8. The system of claim 7, wherein the array of light detectors comprises a SALS detector.

9. The system of claim 8, wherein the array of light detectors comprises a counting detector.

10. The system of claim 9,
    wherein a portion of the one output of light is directed to another part of the flow stream channel.

11. The system of claim 10, wherein signals from the array of light detectors may have velocity information about the core stream.

12. A method for identifying components of a detected light beam having different wavelengths, comprising:
    modulating with a first frequency a first light having a first wavelength;

modulating with another frequency at least another light having another wavelength;

combining the light having the first wavelength with the at least another light with the another wavelength into a light beam;

detecting the light beam with an array of light detectors that converts the detected light into an electrical signal representing light impinging the detector at respective angles and are separated from one another by an area that is not sensitive to light such that each detector subtends its own prescribed angle; and analyzing the electrical signal into signals representing light of the first wavelength and signals representing the at least another light having another wavelength.

13. The method of claim 12, further comprising directing the light beam at a target.

14. The method of claim 13, wherein the target is a core stream of a cytometer flow stream channel.

15. The method of claim 13, wherein the array of detectors detects light scattered by the target.

16. The method of claim 15, wherein the array of detectors are annular detectors.

17. The system of claim 16, wherein the array of detectors has an array of concentric annular detectors.

18. The method of claim 15, wherein the array of detectors comprises an array of individual detectors for determining amounts of light at different angular intervals of direction of the light.

* * * * *

UNITED STATES PATENT AND TRADEMARK OFFICE
CERTIFICATE OF CORRECTION

PATENT NO. : 7,612,871 B2 Page 1 of 1
APPLICATION NO. : 10/931686
DATED : November 3, 2009
INVENTOR(S) : Cox et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1225 days.

Signed and Sealed this

Nineteenth Day of October, 2010

David J. Kappos
*Director of the United States Patent and Trademark Office*